United States Patent [19]
Leaback

[11] Patent Number: 5,096,807
[45] Date of Patent: Mar. 17, 1992

[54] IMAGING IMMUNOASSAY DETECTION SYSTEM WITH BACKGROUND COMPENSATION AND ITS USE

[75] Inventor: David H. Leaback, Radlett, England

[73] Assignee: Murex Corporation, Norcross, Ga.

[21] Appl. No.: 449,502

[22] Filed: Dec. 1, 1989

[30] Foreign Application Priority Data

Mar. 6, 1985 [GB] United Kingdom ............ 8505822
May 13, 1985 [GB] United Kingdom ............ 8512041
Jul. 5, 1985 [GB] United Kingdom ............ 8517042

[51] Int. Cl.⁵ ............ C12Q 1/68; G01N 33/53; C12M 1/40
[52] U.S. Cl. ............ 435/6; 435/7.1; 435/7.4; 435/7.92; 435/288; 435/291; 435/965; 435/973; 436/512; 436/513; 935/77; 935/86; 422/50; 422/52; 422/82.08

[58] Field of Search ............ 435/7.1, 7.4, 7.92, 435/288, 291, 965, 973, 6; 436/512, 513; 935/77, 86; 422/50, 52, 82.08

[56] References Cited

U.S. PATENT DOCUMENTS

| | | | |
|---|---|---|---|
| 3,951,552 | 4/1976 | McCord et al. | 250/211 J X |
| 4,070,578 | 1/1978 | Timothy et al. | 250/207 X |
| 4,476,231 | 10/1984 | Deindoerfer et al. | 436/805 X |
| 4,555,731 | 11/1985 | Zinchuk | 250/213 VT X |
| 4,591,570 | 5/1986 | Chang | 436/519 X |

Primary Examiner—David L. Lacey
Assistant Examiner—William K. Y. Chan

[57] ABSTRACT

The invention provides an imaging immunoassay detection apparatus system and method capable of detecting multiple light emitting reactions from small volume samples simultaneously and quantifying the same.

48 Claims, 2 Drawing Sheets

IMAGING IMMUNOASSAY DETECTION SYSTEM WITH BACKGROUND COMPENSATION AND ITS USE

This is a continuation of application Ser. No. 835,992, filed Mar. 4, 1986, now abandoned.

This invention relates to an imaging immunoassay detection system and method.

BACKGROUND OF THE INVENTION

Highly sensitive instrumentation for immunoassay techniques has been developed to enable measurement of reactions of extremely small quantities of biological and chemical substances. For example, instruments for radioimmunoassay are used which are sensitive, accurate and precise, but require expensive gamma-counting equipment. Other disadvantages of such systems include the short half-life of the radioisotopes, and the danger of using and disposing of the radioactive compounds used in such assays.

Another prevalent technique is the colorimetric enzyme immunoassay which utilises enzymes as labels. An enzyme-linked immunoreactant binds either to an antigen or to an antibody, causing a reaction which yields a quantitative measure of the antibody or antigen, which can be detected by a colour change. Such an assay is usually slower than other conventional techniques involving automated assays.

A third method that can be used is a fluorescence immunoassay, based on the labelling of an antigen or antibody with fluorescent probes. U.S. Pat. No. 4320970 discloses a photon-counting fluorimeter that may be used in such an assay. Disadvantages of such a system include the necessity of processing only one sample at a time. Other systems attempt to use laser beams as the external light source to excite the solution, as disclosed in U.S. Pat. No. 3984533. Again, this system can process only one sample at a time.

Instrumentation for luminescence assays advantageously involves a self-exciting luminescing system, in direct contrast to fluorimeters which utilise an external light source. In general, existing luminometers are complex in operation and require the use of substantial quantities of the reagent being sampled.

Further efforts to analyse more than one reagent sample simultaneously, in a quantitative sense, have not been successful. Efforts toward this end are illustrated by a system described by Schroeder et al in "Immunochemiluminometric Assay for Hepatitis B Surface Antigen", Clinical Chemistry, Vol. 27 No. 8 (1981), wherein a carrier is prepared containing a plurality of reagents for analysis by a luminometer which measures light production during reaction by photo-counting. However, this method and apparatus have the disadvantage of requiring the reactions to be measured sequentially, one at a time. A microprocessor was used to control fluid and air valves for adding the desired chemicals to each well; the carrier was moved in an x-y plan, to position the individual wells sequentially over a phototube, in order to enable the photons emitted by the reaction to be counted. The results were displayed by a printer. Even though photons were counted for 2 seconds at 10 second intervals, obviously a great deal of time would be required to analyse hundreds or thousands of test specimens in sequential order, one at a time.

In addition, GB-A-2132347 discloses a chemiluminometer for simultaneously handling multiple samples. The results obtained, however, are only semi-quantitative.

It has heretofore not been possible to carry out luminescent assays on multiple, small volume samples simultaneously in a short period of time, i.e. seconds. Presently existing technology permits only one such assay at a time and often requires large volume samples, i.e. of 200 $\mu$l or more.

As used herein, the terms "luminescent" and "luminescence" mean all kinds of light emission except incandescence and include chemiluminescence, bioluminescence, prompt fluorescence, delayed fluorescence and phosphorescence and the like.

Rees et al, J. Phys. E: Sci. Instrum. 14 (1981) 229–233, describe a miniature imaging photon detector with a transparent photocathode. It is proposed for use in astronomy and geophysics.

SUMMARY OF THE INVENTION

The present invention overcomes the given drawbacks and provides an imaging immunoassay detection apparatus system and method capable of detecting and quantifying multiple light-emitting reactions from small volume samples simultaneously.

The present invention is very advantageous inasmuch as it is very rapid because it analyses all samples simultaneously, is extremely accurate because it requires no mechanical motion of components, has no repositioning errors as in sequential resolution, can use an internal standard such as a known sample to obtain comparative information, is adaptable with a filter to handle any particular wavelength of light, and is versatile in that it can detect assays requiring external light as well as those that do not require external light, thus being able to operate with immunoassays utilising luminescence and fluorescence and the like.

In brief, the present invention comprises an imaging system for detecting photons generated by chemical reactions comprising sample carrier means having a plurality of individual areas each containing individual chemical reactant samples capable of emitting photons if a reaction takes place, the plurality of reactant-containing areas being arranged in spaced relationship with respect to each other; imaging means associated with said carrier means for simultaneously receiving individual photons emitted from each area sample where a reaction is taking place; and means coupled to the photon-receiving imaging means for generating a signal representing the x-y location of each area sample generating a photon, whereby the reactants in each area sample having a reaction and the number of its photon emissions over any predetermined period of time may be simultaneously identified.

The invention also comprises a method of simultaneously detecting photons generated by a plurality of chemical reactions, comprising the steps of providing a plurality of individual chemical reactant samples each capable of emitting photons when a reaction takes place, the samples being arranged in spaced relationship with respect to each other, and simultaneously detecting the presence and x-y location of each photon emitted from any reacting samples, whereby the total number of photons emitted from each reacting sample over a predetermined period of time may be determined.

Thus, the present invention is not only extremely rapid and processes simultaneously multiple assays, but also enables considerable economies to be made in the use of often expensive reagents concerned because only small quantities of samples are required.

DETAILED DESCRIPTION

The apparatus of the present invention, which will be described in further detail below, may be utilised with any number of different assay techniques as stated earlier, but will be described with particular reference to the use of luminescent immunoassays in the detection of antigen-antibody reactions. More particularly, the invention can be employed to detect the characteristic reactions of labelled monoclonal and polyclonal antibodies with antigens found in samples such as urine, faeces, blood, milk and water and the like.

Polyclonal antibodies are well-known. Monoclonal antibodies may be prepared by the technique first described by Kohler and Milstein, Eur. J. Immunol. 6, 292 (1975). In order to detect the presence of particular antigens, the monoclonal antibodies may be labelled with a multitude of different labels, such as luminescent or fluorescent compounds. Further, the particular labels utilised in the present invention must be capable of emitting light once the antigen-antibody reaction occurs, and thus the reactions are designated as "light-emitting reactions". The present invention will be described in general with reference to a luminescent-labelled monoclonal antibody, although fluorescent labels may also be used as disclosed hereafter. As used herein, the term "reactants" means the combination of (1) a monoclonal antibody labelled with a luminescent or fluorescent compound, and (2) an antigen.

Luminescence is the emission of light by an atom or molecule as an electron is transferred to the ground state from a higher energy state. In both chemiluminescent and bioluminescent reactions, the free energy of a chemical reaction provides the energy required to produce an intermediate reaction or product in an electronically excited state. Subsequent decay back to the ground state is accompanied by emission of light. Biolu- minescence is the name given to a special form of chemiluminescence found in biological systems such as the firefly, in which a catalytic protein or enzyme, such as luciferase, increases the efficiency of the luminescent reaction. When this luciferase enzyme is combined with its substrate, luciferin, in the presence of ATP (adenosine triphosphate), magnesium and oxygen, a flash of light is produced, whose intensity is proportional to the amount of ATP present in the sample. The firefly luciferase/luciferin/ATP system is as follows:

$$ATP \xrightarrow{\frac{Luciferase}{Luciferin}} AMP + PP + h\nu$$

where $h\nu$ is the energy of a photon, $h$ is the Planck constant, and $\nu$ is the frequency associated with the photon.

Assays of the invention can directly determine the number of live organisms in a sample, either because the presence of ATP in a test sample indicated live cells, or because of the presence of immunoglobulins labelled with a luminescence-detectable enzyme (like peroxidase or luciferase).

Chemiluminescent substances such as luminol may also be utilised in a horseradish peroxidase-catalysed oxidation, as follows:

$$luminol \xrightarrow[H_2O_2]{peroxidase} products + h\nu$$

In the present invention, the "light-emitting reactions" generate photons which are coupled to an imaging device such as an imaging photon detector, a charge-coupled device, or a vidicon tube (any of a variety of camera tubes having a photoconductive target). In the preferred embodiment, an imaging photon detector is used.

In particular, the reactions may be generated by reactants spatially arranged in individual areas on a sample carrier in a single row or column or by a two-dimensional array of reactants spatially arranged, for instance, in rows and columns. For example, a carrier may have an array, such as rows, of 1 mm outside diameter nylon tubes containing the labelled monoclonal antibodies, to which is added the specimen or specimens being tested for the presence of an antigen. The fluids involved are self-contained and of a very small volume. Thus, an advantage of the present invention is that the imaging photon detector can quantify (in 10 seconds or less) light emitted from multiple "light-emitting reactions", in volumes of 3 µl or less, i.e. much smaller than can be used in known apparatus.

Another carrier suitable for use with an imaging photon detector is a microtiter plate with multiple samples in rows and columns. A particular plate may contain as many as 96 individual wells. Each well contains different labelled monoclonal antibodies adsorbed on the surface of the plate. A portion of the specimen is added to each well. The presence and quantity of a particular antigen in an individual well is determined by the number of photons generated by the antigen-antibody reaction.

A third carrier involves the principle of using immobilised antibodies on a plurality of filaments; labelled monoclonal antibodies are immobilised in individual areas on a plurality of filaments. Each filament may bear a different labelled monoclonal antibody capable of emitting light upon the detection of an antigen. Because the reactions on the individual filaments generate light, the imaging photon detection system can quantitatively determine the presence of particular antigens.

The present invention envisages the use of any number of different types of multiple, chemically-produced, light-emitting reactions which can be imaged by the image photon detector. As the samples emit light, the present invention counts the individual photons impinging upon a light sensitive photocathode of an imaging photon detector.

Each of the above means for containing a plurality of reactants can be used in the apparatus system described below, in which the container is identified as the specimen carrier means.

The apparatus system will be described with reference to FIGS. 1 and 2.

Figure 1:
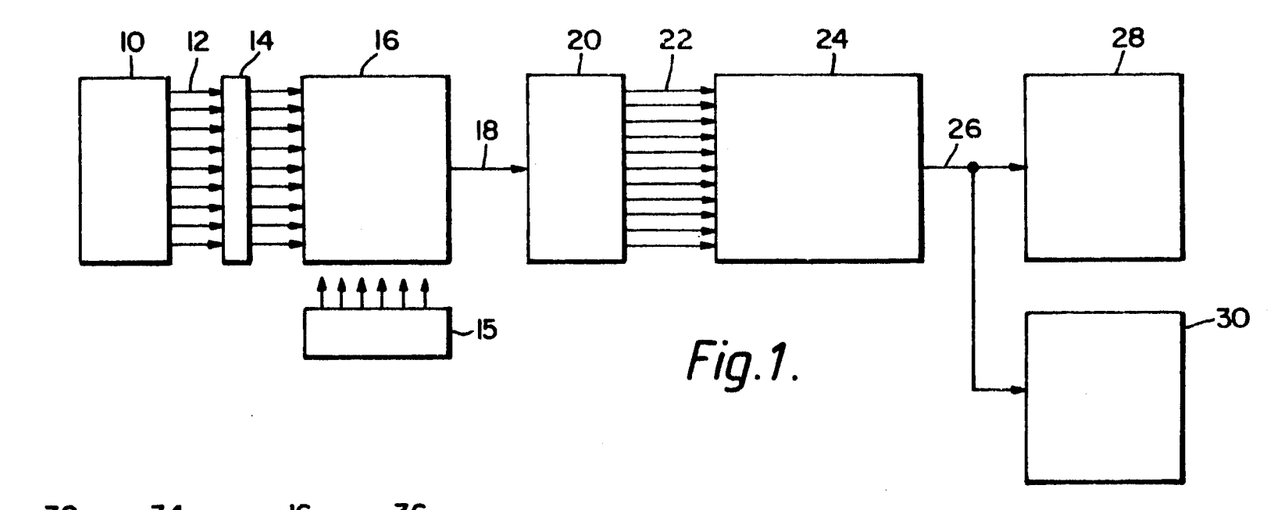
FIG. 1 is a diagrammatic representation of the novel photon detection system.

FIG. 1 is a system for quantitative assay analysis of multiple biochemical images using an imaging photon detector. The system enables the detection of very low concentrations of substances present in fluid samples or specimens which, in the course of their reaction, emit light photons under certain conditions. In particular, the system has demonstrated sensitivity in the order of $10^{-16}$ and lower.

Figure 3:
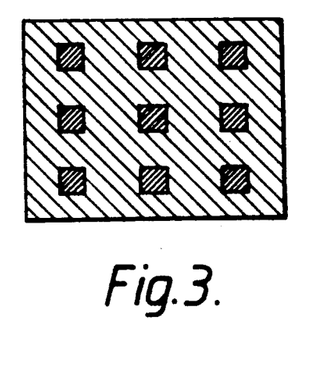
FIG. 3 is a representation of both background noise signals and signals from discrete areas of reaction (whereby the background noise signals may be cancelled, leaving only reaction signals)
Figure 4:
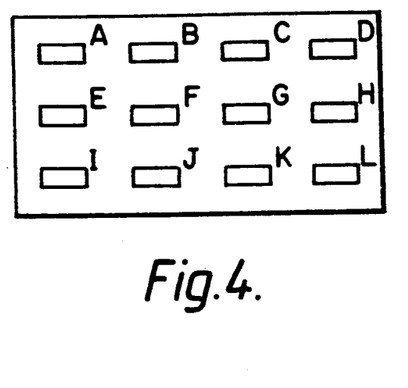
FIG. 4 represents a carrier in which multiple antibody labels may be used simultaneously or in which a standard reaction may be compared with other reactions.

FIG. 1 shows a specimen carrier means 10 which may include a plurality of fluid samples all capable of simultaneously undergoing a reaction. Samples can be spaced in individual areas as a row or column or in a two-dimensional array of rows and columns as shown in FIG. 3 and FIG. 4, for example only. The reactions that produce light generate photons 12 which are focused by an optical system 14 to form the image of the light outputs of each of the samples on a photoconductive target forming a portion of an imaging photon detector (IPD) 16. The imaging photon detector 16 will be disclosed in detail hereinafter but is known in the art; it immediately converts incoming light into quantitative information which can be stored and processed within a memory of any conventional computing means such as a microprocessor 24.

The imaging detector 16 of the present invention takes simultaneous readings of discrete sample areas such as the small darker shaded orthogonal areas of FIG. 3 rather than averaging the readings of the entire sample area (including the carrier area surrounding the sample). Background noise, represented by the shading lines in FIG. 3, is caused by non-specific binding antigens or antibodies to the solid surface of the carrier, which are not washed away in the preparation of the carrier. Conventional detectors read these signals generated by this undesirable binding and, because these conventional detectors average the signal over the entire sample area, they interpret these undesired false signals as a positive reaction. Background noise effectively decreases the sensitivity of the assay at relatively low levels of concentration, where the positive reaction signal has nearly the same intensity level as the background noise.

Figure 6:
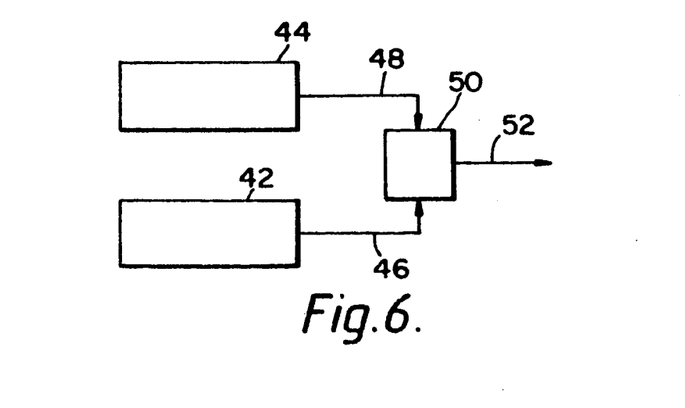
FIG. 6 is a schematic representation of a circuit in a microprocessor for subtracting background noise from the sample signals to obtain an output signal representing substantially only pure photon emission from a reactant sample.

The present invention eliminates the background noise problem by simultaneously reading the signal from the background environment and the signal from the concentrated reaction area and comparing the two readings. Because the present imaging immunoassay detection system can read signals from numerous discrete reaction areas at the same instant, a real time measurement of the signals from the discrete areas of reaction in a two-dimensional array can be taken, averaged, and compared with the signal representing the background noise caused by the non-specific binding. The computer 24 can analyse and display the results by subtracting from the signals representing the discrete areas of reactions the signals representing the background noise, as shown in FIG. 6, thereby leaving the pure reaction signals.

Further, since the present system can simultaneously evaluate a carrier, such as a 96-well microtiter tray, without repositioning the carrier or tray as in systems using sequential detection, resolution errors that occur from imprecise mechanical repositioning of the samples between measurements as required in the prior art are eliminated.

Since the present imaging immunoassay detection system can look at more than one discrete reaction at a time, contrasting reactions can be analysed relative to one another. By way of illustration, in a two-dimensional array of samples as in a microtiter tray represented in FIG. 4, reactions can be compared side-by-side simultaneously. The amount of photons generated by each reaction can be read and analysed by computer 24 and the relative extent of reaction compared. In this way, a more accurate comparison can be made between specific samples, thus providing better test results. As an example, a negative reaction may be placed in a discrete area A in FIG. 4, to serve as a control for purposes of comparison with a positive reaction in a discrete area B. The negative reaction in discrete area A may still generate spurious signals caused by non-specific binding, as pointed out earlier. This background noise level is potentially constant across a given carrier such as a microtiter tray and is useful in setting up a base level of signal generation from which more positive reaction can be compared.

Thus, the present imaging system is capable of rapid quantitative analysis of samples. Because of its unique ability to simultaneously read and analyse numerous samples, the time necessary to produce results is dramatically reduced.

Furthermore, the sensitivity of the present imaging system allows for very accurate measurements even at very low concentrations of the samples. For instance, an imaging photon detector is capable of measuring individual photons of light. By using amplifiers, the system is able to register very low concentrations of materials and is therefore useful in areas such as diagnosing for the presence of infectious organisms, as well as drug monitoring and disease detection.

Because of its sensitivity, the imaging system can not only detect minute quantities of a reaction samples, but can also read a very small area of reaction. Thus, the amount of reagent and the area which are needed to conduct the assay are less then before, thereby minimising the cost of reagents and carrier materials.

The output of the imaging photon detector 16 on line 18 comprises analog signals which represents the x-y spatial correspondence of each detected photon, thus identifying electrically the x-y address of the sample or specimen that produced the light. These analog signals are coupled to an analog-to-digital (A/D) converter 20 which produces digital output signals on lines 22 representing the spatial orientation of the specimen source producing the photon received by the imaging photon detector 16 and thus identifying the particular sample or specimen which produces the photon. The digital signals 22 are coupled to a microprocessor 24 which stores and analyses the image information and can be programmed to display it in any desired format. The reactions continue to generate light throughout any desired predetermined period of time, e.g. as little as 10 seconds or less, and the number of photons produced by each reacting sample is accumulated in the memory of microprocessor 24. Thus, microprocessor 24 produces signals on line 26 to video display 28 and printer 30 for visual display and analysis of the light received, and accumulated, from samples 10.

A bar chart may be displayed on video terminal 28 which identifies each of the samples and illustrates the relative amount of light or number of photons being generated by each sample. Such a bar chart could also be produced, for a permanent record, by printer 30.

Also, a two-dimensional image of the array of samples as they are physically located (i.e. their x-y address) can be produced, the intensity of the light generated by each sample being indicated either in colour or by numerals, thus identifying which sample is generating the greatest amount of light. Obviously, the microprocessor 24 can perform any operation on the samples as desired to correct and calibrate the image and to compensate for any inherent noise in the system such as by subtracting the background noise, as explained earlier. Noise also may be reduced by cooling the imaging photon detector 16 with a cooling unit 15 in any well known manner such as by circulating a cooling liquid or a refrigerant about the imaging photon detector 16. Cooling the detector 16 reduces the tendency for free electrons to be emitted from elements of the detector 16, and which assist in generating the background noise.

Figure 2:
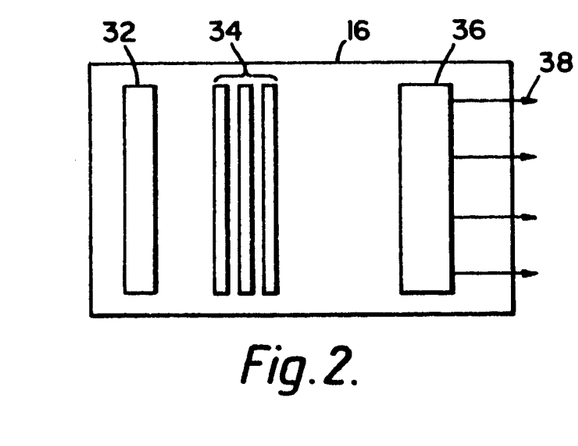
FIG. 2 is a diagrammatic representation of the imaging photon detector used in the system of FIG. 1.

FIG. 2 is a diagrammatic representation of the construction details of the imaging photon detector used in the preferred embodiment herein and which is known in the art. The detector may be type IPDG1 or type PIDF1 manufactured by Instrument Technology Limited in East Sussex, England. The imaging photon detector 16 is a two-dimensional imaging sensor capable of detecting extremely weak radiation, e.g, capable of detecting an ATP content in the sample down to as low as $10^{-16}$ moles/sample. As indicated earlier, that image is produced in analog form which is converted through an analog-to-digital converter 20 to a digital form for use by the microprocessor 24.

Light is composed of individual photons. Each individual photon has an extremely small amount of energy associated therewith. In most common images, the light contains fluxes of millions or billions of photons per square centimeter and per second. Using the imaging photon detector 16, each incoming photon has a high probability of detection by the photocathode 32.

The photoconductive target 32 can thus be thought of as equivalent to a photographic film except that it has a sensitivity of the order of 100 times greater. When a photon strikes the light sensitive photocathode 32, a photoelectron is released from photocathode 32 and is immediately accelerated into a series of microchannel plate intensifiers or amplifiers 34. As a result of the intensification created by microchannel plates 34, a gain in the range of $3 \times 10^6$ to $3 \times 10^7$ electrons is emitted from the rear of each microchannel plate for each incident photoelectron and thus corresponds to each initially detected photon. The combination of the microchannel plates 34 thus enables extremely small amounts of light to be detected.

A resistive anode encoder 36 located immediately behind the microchannel plates 34 translates the electron burst into signals which can be processed easily into a two-dimensional x-y address of the detected photon and thus the sample. Thus, the analog readout of the resistive anode 36 on line 18 in FIG. 1 is used to present a linear x-y registration of each photoelectron event. The read-out through four orthogonal electrodes 38 is suitably processed to provide digital representation of the x-y position of the incident photoelectron (and thus the sample) by analog-to-digital converter 20 and microprocessor 24, both shown in FIG. 1. Thus, by the use of the imaging photodetector 16, the full image of all of the samples 10 in two dimensions is created by integrating the image focused onto the photocathode 32, photon-by-photon. Thus, the present system detects and presents information relating to multiple imaging, presents the information immediately upon the occurrence of the emitted light, detects extremely small amounts of light down to and including a single photon, and quantifies such information for each specific x-y sample or specimen address.

Instead of an imaging photon detector (which is preferred), the system may use a charge-coupled device (CCD) as the imaging device 16. CCD's are well known in the art. They are used in conjunction with an optical lensing system (such as optical system 14 in FIG. 1) which focuses light from the object being investigated (sample array 10 in FIG. 1) on to the CCD. Varying amounts of light from individual samples are incident on individual pixels within the CCD and charge the pixels to different levels proportional to the incident light. Thus the optical information or light from sample array 10 is available in analog form across the pixels of CCD array 16. The analog information is then shifted out of the CCD and converted to digital form in a well known manner by the analog-to-digital converter 20 and is then coupled to a memory in computer 24 where the various measurement levels and comparisons can be made by appropriate manipulation of the digital information. See "Imaging", The Optical Industry and System Purchasing Directory, 1983, pp. E-72 to E-74.

As is well known in the prior art, the individual pixels within a CCD array are closely spaced and arranged horizontally in rows and vertically in columns so that a given CCD imaging device 16 provides a fixed number of pixels of information. For instance, some CCD's have 320 vertical columns of pixels and 512 horizontal rows of pixels.

CCD's have several characteristics which make them advantageous in the present invention as an imaging device. CCD's are small and rugged and have closely spaced pixels and are therefore useful where, as here, precise measurements are required. They also receive an image by the direct reception of light energy without being scanned, and store the received data until the data are transferred to another storage device. Further, the data received from the CCD can be processed by simple comparison or detection techniques, thereby avoiding complex and major time-consuming sampling techniques ordinarily used to process such data.

Another imaging device which can be used instead of an imaging photon detector or a CCD is a vidicon tube. The name vidicon is generally applied to any of a variety of tubes having a photoconductive target. The vidicon operates in a well known manner and utilises an electron beam to scan a light-sensitive photoconductive target. A transparent conductive layer applied to the front side of the photoconductor serves as a signal or target electrode. The target electrode is operated at a positive voltage with respect to the back side of the photoconductor which operates at cathode (near zero) voltage. In operation, the scanning beam initially charges the back side of the target electrode to cathode potential. When a light pattern (light photon) is focused on the photoconductor, its conductivity increases in the illuminated areas and the back side of the target charges to more positive values. The electron beam then reads the signal by depositing electrons on the positively charged areas, thereby providing a capacitively coupled signal at the signal output electrode. See "Imaging Devices", RCA Solid State Devices, 19, pp. 3-9.

Thus, as used in FIG. 1, a vidicon 16 receives the photons or light output from the respective reactions through optics 14 and produces the analog output on line 18 as described earlier. The analog output on line 18 is coupled to the analog-to-digital converter 20 from which digital signals are processed in the same manner as for the imaging photon detector.

Figure 5:
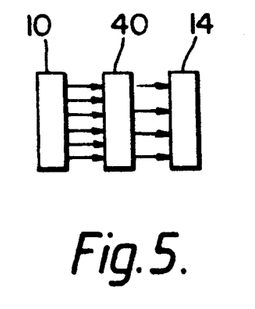
FIG. 5 is a diagrammatic representation of how a wavelength interference filter may be used with the carrier of FIG. 4 to pass only a particular light wavelength, thereby allowing only photons of a particular wavelength corresponding to a labelled antibody to pass to the imaging detector.

It is also possible to use multiple antibody labels with the imaging immunoassay detection system of the present invention. Different antibodies are labelled with different indicators and correspond to different discrete areas on the carrier medium. Thus, with regard to FIG. 4, discrete area A may have an antibody labelled with an indicator such as luciferase, discrete area B may have an antibody labelled with an indicator such as a bacterial reductase, and so forth. Since each indicator generates a different wavelength of light, each discrete area of each antibody has its own particular wavelength of light which can be detected by imaging device 16. As can be seen in FIG. 5, a wavelength interference filter 40 of the desired characteristics is placed between samples 10 and optics 14 such that only photons of a particular wavelength corresponding to an antibody labelled with a particular indicator pass through to the imaging detector 16. In this manner, the novel imaging immunoassay detection system can be made wavelength selective, thereby permitting greater flexibility and sensitivity.

Figure 7:
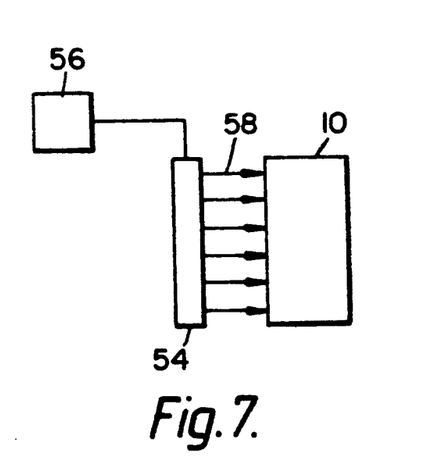
FIG. 7 is a diagrammatic representation of the use of invisible ultraviolet radiation as a source of external light.

It will be understood, of course, that if a fluorescing material, such as fluorescein, is used as the label, invisible ultraviolet light or black light will have to be used. FIG. 7 illustrates such apparatus, wherein an ultraviolet light source 54 is powered by an appropriate power source 56. Ultraviolet light rays 58 impinge on samples in carrier 10 which fluoresce if a reaction takes place. The remainder of the circuit operates as described above in connection with FIG. 1.

As shown in FIG. 6, the signals detected by imaging device 16, representing background noise and sample signals combined, are stored in a memory 42 of microprocessor 24. The detected signals representing background noise alone are stored in a memory 44 of microprocessor 16. By coupling these two stored signals on lines 46 and 48 to an arithmetic unit 50, and subtracting one from the other an output signal is obtained on a line 52, which represents substantially only pure photon emission from any selected reactant sample. Thus, background noise is substantially eliminated or minimised.

The system of the present invention can be used in conjunction with labelled DNA or RNA probes instead of antibodies as a diagnostic tool. DNA probes or RNA probes are specific sequences of nucleotides that are complementary to particular sequences of a sample piece of DNA or RNA. These probe pieces of DNA or RNA can be labelled with an indicator so as to generate a signal, analogous to an immunoassay, and would be contained in a carrier 10 such as shown in FIG. 1. In use, the DNA or RNA is first removed from a cell or other structure in a sample containing a DNA or RNA sequence. The DNA or RNA is bound to a surface such as nitrocellulose, and is then denatured so that its complementary strands are separated. The DNA or RNA probe, labelled with an indicator, is then added to the sample and, if the specific complementary sequence of the probe is present in the sample, the sample and probe will combine. The unbound label is washed away and the sample containing bound labelled probe is read in the manner described hereinabove with reference to FIG. 1.

Isotope-labelled assays are also within the scope of the present invention. In such an assay, the indicator component is labelled with an isotope, such as phosphorus-32 or iodine-125, which emits gamma radiation. In the performance of a radioisotopic assay, the isotope-labelled component, typically an antibody, is bound to the analyte of interest, the unbound label is washed away from the reaction zone, and the zone is read. The reading of the central reaction zone is accomplished in this embodiment by the incorporation of a phosphor screen. Phosphor screens are well known in the art and are used to convert electron energy into radiant energy. These screens are composed of a thin layer of luminescent crystals, phosphors, which emit light when bombarded by electrons. In the present case, the phosphor screen receives gamma radiation from the labelled analyte and, in turn, emits photons which are received by the detection system. Thus, in FIG. 1, carrier 10 would be the phosphor screen which received electrons from any reaction and emits light 12 which is focused by optics 14 and processed in the manner explained previously. In this manner, gamma particles are converted into detectable photons which are received and processed as described hereinabove. Other types of gamma-to-photon conversion means are also usable and within the scope of the present invention.

As an illustration of the sensitivity of the IPD array detector system, the well established firefly luciferase/luciferin-based assay for ATP provides a useful reference. Thus, using the standard "Lumac" firefly luciferase/luciferin reagents for the bioluminescent ATP assay in the Lumac Biocounter luminometer, the lower limit for the assay (carried out as recommended by the manufacturer) is set by the "background" count of photons (of about 10/second) typically experienced. This sets the lower limit of the determination at about $5 \times 10^{-15}$ moles ATP per sample. In contrast, using the IPD system described above, the lower limit of the determination, using similar criteria, is set at about $5 \times 10^{-17}$ moles ATP.

The invention will be further illustrated in conjunction with the following Example, which is set forth for purposes of illustration only and not by way of limitation.

EXAMPLE

Monoclonal antibodies are prepared according to the method of Kohler and Milstein noted above. In particular, an antibody to Shigella is prepared by the procedure described in WO-A-86/00296 and labelled with luminescent compounds such as the firefly luciferase/luciferin/ATP system. These luminescent labelled antibodies are then adsorbed onto the surface of a microtiter tray. Additionally, each well of the tray may contain labelled monoclonal antibodies to different antigens, thus allowing diagnosis for the presence of a wide variety of different antigens at the same time. This microtiter tray thus contains a number of known antibodies at known x-y addresses or areas on the tray. The tray is then washed with the specimen containing the unknown antigen(s) and an antigen-antibody reaction occurs. Next, the tray is rinsed and unbound antibodies are removed. Then, the tray is placed in the specimen carrier holder of the imaging photon detecting system described above. The presence and amount of the unknown antigen(s) in the specimen are determined by the photons generated by the characteristic antigen-antibody reactions and their x-y location on the microtiter tray.

While the invention has been described in connection with a preferred embodiment, it is not intended to limit the scope of the invention to the particular form set forth, but, on the contrary, it is intended to cover such alternatives, modifications and equivalents as may be included within the spirit and scope of the invention as defined by the appended claims.

What is claimed is:

1. A system for detecting photons generated by chemical reactions comprising:
   a. sample carrier means having a plurality of individual discrete separated areas each containing a separate and independent chemical reactant sample which will emit a number of light photons when a reaction takes place, said plurality of reactant-containing discrete separated areas being arranged in two-dimensional spaced relationship with respect to each other and having spaces therebetween;
   b. photon-receiving means associated with said sample carrier means for simultaneously receiving individual photons emitted from each discrete area sample and from said spaces when photons are emitted from said spaced; and
   c. signal generating means coupled to said photon-receiving means for generating signals representing a location of each of said discrete area sample and each of said spaces generating a photon, whereby the sample location of each area having a reaction, the location of each of said spaces generating a photon and said number of their photon emissions over any predetermined period of time will be simultaneously identified.

2. A system as in claim 1 wherein:
   a. said photon-receiving means is constructed so as to respond to photons emitted from said spaces for generating signals representing background noise which consists of emitted light photons from said spaces between said chemical reactant samples; and
   b. wherein there is included means for subtracting said background noise signals from said signals representing photon emission from each of said samples to produce a resulting signal whereby said resulting signal represents substantially only pure emissions from said reactant samples.

3. A system as in claim 1 further including:
   a. computing means coupled to said signal generating means for receiving and storing each of said signals whereby said location of each of said spaces generating a photon and the number of photons generated by each of said spaces and each sample having a reaction over said any predetermined period of time can be accessed; and
   b. display means coupled to said computing means for presenting a representation of each of said samples and the number of its photon emissions.

4. A system as in claim 2 further including:
   a. computing means coupled to said signal generating means for receiving and storing each of said signals whereby said location of each of said spaces generating a photon and the number of photons generated by each of said spaces and each sample having a reaction over said any predetermined period of time can be accessed; and
   b. display means coupled to said computing means for presenting a representation of each of said samples and the number of its photon emissions.

5. A system as in claim 3 wherein said display means is a video display.

6. A system as in claim 4 wherein said display means is a printer.

7. A system as in claim 3 wherein said computing means is a microprocessor.

8. A system as in claim 1 wherein said signal generating means is a photomultiplier tube having a photoconductive target for producing reaction location output signals representing the number of photons emitted by each reaction, and the space output signals representing the number of photons emitted by said spaces.

9. A system as in claim 1 wherein said signal generating means is a charge coupled device for producing reaction location output signals representing the number of photons emitted by each reaction, and the number of photons emitted by said spaces.

10. A system as in claim 1 wherein said signal generating means is a vidicon tube for producing reaction location output signals representing the number of photons emitted by each reaction and the number of photons emitted by said spaces.

11. A system as in claim 4 wherein each of said chemical reactant samples comprises:
    a. an antibody;
    b. an antigen; and
    c. an indicator which labels said antibody and which generates said photons of light when a reaction occurs between said antibody and said antigen.

12. A system as in claim 3 wherein at least one of said chemical reactant samples contains an indicator which emits light of different wavelength than others of said chemical reactant samples.

13. A system as in claim 12 further comprising:
    a. a photoconductive target forming a portion of said signal generating means; and
    b. an optics system constructed so as to focus light photons from said reactant samples on said photoconductive target to generate said sample location output signals representing the number of said photon emissions from each said sample.

14. A system as in claim 13 further comprising a specific wavelength light interference filter positioned between said sample carrier means and said optics system for passing only a specific light wavelength corresponding to said at least one chemical reactant indicator being said indicator which emits light of different wavelength than said others of said chemical reactant samples whereby only said at least on chemical reactant is monitored by said system for photon emission.

15. A system as in claim 2 wherein said photon emitting reactant samples are arranged in discrete areas forming a single row or column.

16. A system as in claim 2 wherein said photon emitting reactant samples are arranged in discrete areas forming a two-dimensional array of rows and columns.

17. A system as in claim 15 or 16 further including:

a. a first reactant sample in one of said discrete areas;
b. a second different reactant sample in a second one of said discrete areas; and
c. means for comparing signals representing light photons emitted from said second reactant sample with signals representing light photons emitted from said first reactant sample, whereby one reactant sample may be compared with another.

18. A system as in claim 17 wherein said second reactant sample is a test sample and said first reactant sample is a control sample representing a desired standard control reaction, whereby said test sample may be compared with said control sample.

19. A system as in claim 2 wherein:
a. said signals generated by said signal generating means include photon representation analog signals severally representing the numbers of photons generated by each photon-generating sample over a predetermined period of time, and further including
b. an analog-to-digital converter coupled to said signal generating means for converting said analog signals representing said numbers of photons to digital signals;
c. a microprocessor coupled to said analog-to-digital converter; and
d. storage means in said microprocessor having a plurality of locations therein corresponding to said plurality of reactant samples for storing said digital signals.

20. A system as in claim 2 wherein each of said chemical reactant samples comprises:
a. a sample containing a sequence of nucleic acids;
b. a nucleic acid probe specific for its complementary sequence in nucleic acids respectively; and
c. an indicator which labels said nucleic acid probe and which generates said photons of light when a reaction occurs between said probe and its said complementary sequence.

21. A system as in claim 2 wherein each of said chemical reactant samples comprises:
a. an isotope-labeled antibody;
b. an analyte of interest whereby when a reaction occurs between said labeled antibody and said analyte of interest, gamma rays are generated; and
c. a phosphor screen for receiving said gamma rays and generating said photons of light.

22. A system as in claim 1 wherein:
a. said photon receiving-means is constructed so as to respond to photons emitted from said spaces for generating signals representing background noise which consists of emitted light photons from said spaces between said reactant samples; and
b. wherein there is included means for substracting said background noise signals from said signals representing photon emission from each of said samples whereby the resulting signal represents substantially only pure emissions from said reactant samples.

23. A system as in claim 22 further including:
a. computing means coupled to said signal generating means for receiving and storing each of said signals whereby the location and number of photons generated by each of said spaces and each sample having a reaction over said any predetermined period of time can be accessed; and b. display means coupled to said computing means for presenting a representation of each of said samples and the number of its photon emissions.

24. A system as in claim 23 wherein said display means is a video display.

25. A system as in claim 23 wherein said display means is a printer.

26. A method of detecting photons generated by a chemical reaction comprising:
a. proving a plurality of discrete separated individual and independent chemical reactant samples each capable of reacting with a specific substance and emitting light photons when a reaction takes place, said reactant samples being arranged in two-dimensional spaced apart relationship with each other;
b. creating spaces of predetermined size between said reactant samples, said spaces emitting spurious photons representing background noise;
c. adding to each of said samples a specimen potentially containing at least one unknown specific substance such that a reaction generating photons occurs when said specific substance is present in said specimen;
d. simultaneously generating first signals detecting presence of each photon emitted within each of said spaces and from any of said samples and a location of each of said reactant samples from which a photon is emitted, whereby a total number of photons emitted from said spaces and from each individual reactant sample over a predetermined period of time will be determined, and generating a background signal representing background noise.

27. A method of detecting photons generated by a chemical reaction as in claim 26 further including accumulating the number of photons emitted by any reactant samples over a predetermined period of time whereby the total photon emission of any reactant sample may be determined.

28. A method of detecting photons generated by a chemical reaction as in claim 26 further including subtracting said signal representing background noise from said first signals thereby to create other signals representing pure emissions from said reactant samples.

29. A method of detecting photons generated by a chemical reaction as in claim 26 further including storing in a microprocessor numbers severally corresponding to the numbers of photons emitted by said reactant samples over a predetermined period of time, thereby enabling the photon emissions of any reactant sample to be compared with the number of photon emissions from other reactant samples.

30. A method of detecting photons generated by a chemical reaction as in claim 29 further including displaying for each reactant sample a representation of the total accumulation of the number of photons emitted by that sample over a predetermined period of time thereby giving a visual indication of the number of photons emitted by said each reactant sample over said predetermined period of time.

31. A method for detecting a reaction comprising:
a. locating a plurality of labeled compounds onto discreet and separated areas of a carrier;
b. adding to at least one of said labeled compounds a specimen potentially containing at least one unknown substance of a type which produces a reaction with said at least one of said labeled compounds when said unknown substance is present and comprises a particular substance, any said reaction generating light photons;

c. individually detecting any of said reaction that may occur by simultaneously detecting location of any said reaction and number of light photons emitted by each said reaction;

d. detecting any spurious photons emitted in spaces between said discreet and separated areas of said carrier and generating from said spurious photons a background noise signal representing background noise for said carrier; and e. adjusting said number of photons thereby to essentially eliminate any noise component therefrom.

32. A method as in one of claims 26 31 wherein said at least one unknown substance is an antigen and further comprising contacting at least a portion of said specimen with a labeled monoclonal antibody.

33. A method as in claim 26 further including utilizing an imaging detector to detect presence and location of each photon emitted by any of said reacting samples.

34. A method as in claim 33 further including utilizing an imaging photon detector as said imaging detector.

35. A method as in claim 33 further including utilizing a charge coupled device as said imaging detector.

36. A method as in claim 33 further including utilizing a vidicon tube as said imaging detector.

37. A method as in claim 26 further comprising forming each of said reactant samples with an antibody, an antigen, and an indicator which labels said antibody and which generates said light photons when a reaction occurs between said antibody and said antigen.

38. A method as in claim 37 further including forming at least one of said chemical reactants with an indicator which emits light of different wavelength than others of said chemical reactants indicators.

39. A method as in claim 38 further including:
a. forming a portion of said photon detecting means as a photoconductive target; and
b. focusing said light photons from said reactant samples on said photoconductive target with an optics system to generate signals representing presence and location of said photon emissions from said samples.

40. A method as in claim 39 further including positioning a specific wavelength light interference filter between said reactant samples and said optics system for passing only a specific light wavelength corresponding to said at least one of said chemical reactants indicators being said indicator which emits light of different wavelength than the others of said chemical reactants indicators whereby only said at least one chemical reactants is monitored by said system for photon emission.

41. A method as in claim 26 further including:
a. detecting background noise signals consisting of said spurious light photons emitted from said spaces between said reactant samples; and
b. subtracting said background noise signals from said signals representing photon emissions from each of said samples whereby a resulting signal represents substantially only pure photon emissions from said reactant samples.

42. A method as in claim 26 further comprising arranging said photon emitting reactant samples in discrete areas forming a single linear sequence of either a row or column.

43. A method as in claim 26 further comprising arranging said photon emitting reactant samples in discrete areas forming a two-dimensional array of rows and columns.

44. A method as in claim 42 or 43 further comprising:
a. placing a first reactant sample in one of said discrete areas;
b. placing a second different reactant sample in a second one of said discrete areas; and
c. comparing signals representing the number of light photons emitted from said sample in said second one of said areas with said signals representing light photons emitted from said first sample whereby one sample may be compared with another.

45. A method as in claim 44 further comprising:
a. forming said first sample of reactants providing a desired standard control reaction; and
b. forming said second reactant sample as a test sample whereby said test sample may be compared with said control sample.

46. A method as in claim 26 wherein the step of generating first signals detecting the presence of each photon emitted and the location of each of said reactant samples from which a photon is emitted is the step of generating analog signals.

47. A method as in claim 46 further including:
a. converting said analog signals to digital signals;
b. coupling said digital signals to a microprocessor; and
c. storing said digital signals in a plurality of memory locations in said microprocessor.

48. A method of detecting photons generated by a chemical reaction as in claim 26 further including the step of subtracting said background signal representing background noise from said first signals thereby to create other signals representing pure emissions from said reactant samples.

* * * * *

UNITED STATES PATENT AND TRADEMARK OFFICE
CERTIFICATE OF CORRECTION

PATENT NO. : 5,096,807
DATED : March 17, 1992
INVENTOR(S) : David H. Leaback It is certified that error appears in the above-identified patent and that said Letters Patent is hereby corrected as shown below:

On the title page, item [30] Foreign Application Priority Data: Correct "Foreign Application Priority Data" to include: --March 16, 1985 (GB) United Kingdom ... 8,506,865.--

Signed and Sealed this

Fifth Day of April, 1994

*Attest:*

BRUCE LEHMAN

*Attesting Officer*     *Commissioner of Patents and Trademarks*